United States Patent
Weber et al.

(10) Patent No.: US 11,279,685 B2
(45) Date of Patent: Mar. 22, 2022

(54) ENANTIOMERIC SEPARATION OF RACEMIC NICOTINE BY ADDITION OF AN O,O"-DISUBSTITUTED TARTARIC ACID ENANTIOMER

(71) Applicants: SIEGFRIED AG, Zofingen (CH); CONTRAF-NICOTEX-TOBACCO GMBH, Heilbronn (DE)

(72) Inventors: Beat Theodor Weber, Zofingen (CH); Ben Pan, Nantong (CN)

(73) Assignees: SIEGFRIED AG, Zofingen (CH); CONTRAF-NICOTEX-TOBACCO GMBH, Heilbronn (DE)

( * ) Notice: Subject to any disclaimer, the term of this patent is extended or adjusted under 35 U.S.C. 154(b) by 0 days.

(21) Appl. No.: 16/956,964

(22) PCT Filed: Dec. 18, 2018

(86) PCT No.: PCT/EP2018/085444
§ 371 (c)(1),
(2) Date: Jun. 22, 2020

(87) PCT Pub. No.: WO2019/121649
PCT Pub. Date: Jun. 27, 2019

(65) Prior Publication Data
US 2020/0331883 A1    Oct. 22, 2020

(30) Foreign Application Priority Data

Dec. 22, 2017 (EP) .................... 17210181

(51) Int. Cl.
*C07D 401/04*    (2006.01)
(52) U.S. Cl.
CPC .................. *C07D 401/04* (2013.01)
(58) Field of Classification Search
CPC .................................................. C07D 401/04
See application file for complete search history.

(56) References Cited

U.S. PATENT DOCUMENTS

| 8,378,111 | B2* | 2/2013 | Divi ...................... C07D 401/04 |
| | | | 546/279.4 |
| 8,884,021 | B2 | 11/2014 | Tian et al. |
| 9,556,142 | B2 | 1/2017 | Arnold |
| 2006/0135617 | A1 | 6/2006 | Kamiyama et al. |
| 2012/0209006 | A1 | 8/2012 | Divi et al. |
| 2014/0031554 | A1 | 1/2014 | Tian et al. |
| 2016/0326134 | A1* | 11/2016 | Willis .................. C07D 213/80 |
| 2020/0331884 | A1 | 10/2020 | Weber et al. |

FOREIGN PATENT DOCUMENTS

| CN | 102617547 | 8/2012 |
| EP | 2 484 673 | 8/2012 |
| EP | 2 487 172 | 8/2012 |
| JP | 2003342259 | 12/2003 |
| JP | 2006335639 | 12/2006 |
| WO | WO 2012/100722 | 8/2012 |
| WO | WO 2016/065209 | 4/2016 |

(Continued)

OTHER PUBLICATIONS

Aceto M. D., et al., J. Med. Chem., 1979, vol. 22, No. pp. 174-177.
Berichte der deutschen chemischen Gesellschaft, vol. 37, 1904, pp. 1225-1235.
Bowman E.R. et al., Synthetic Comm., 1982, vol. 12, No. 11, pp. 871-879.
Chavdarian C. G. et al., J. Org. Chem.,1982, vol. 41, 1069-1073).
Hatton et al. (2009) Synthesis of four racemic nicotine isotopomers doubly labelled with stable isotope. J. Label Compd. Radiopharm. 52:117-122.
International Preliminary Report on Patentability corresponding to International Patent Application No. PCT/EP2018/085437 dated Jun. 23, 2020.

(Continued)

*Primary Examiner* — Patricia L Morris
(74) *Attorney, Agent, or Firm* — Jenkins, Wilson, Taylor & Hunt, P.A.

(57) ABSTRACT

The present invention relates to a method of separating racemic nicotine of Formula (1-a) as a mixture of the (R)- and (S)-enantiomers into the enantiomerically pure (S)- and (R)-nicotine represented by Formula (1-b) and (1-c), by adding a mixture of the L- and the D-enantiomer of a O,O'-disubstituted tartaric acid, wherein the molar ratio of the L- to the D-enantiomer is from 80:20 to 95:5, and obtaining the (S)-nicotine of formula (1-b), or by adding O,O'-dibenzoyl-D-tartaric acid and obtaining the (R)-nicotine of formula (1-c).

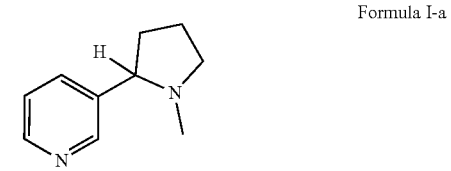

mixture of (R)- and (S)-Nicotine    Formula I-a

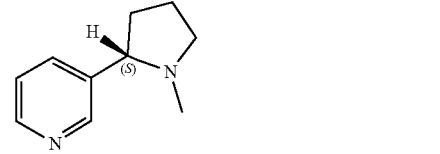

(S)-Nicotine    Formula I-b

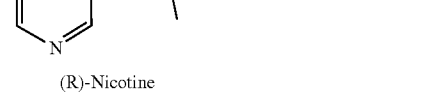

(R)-Nicotine    Formula I-c

14 Claims, No Drawings

(56) References Cited

FOREIGN PATENT DOCUMENTS

| WO | WO 2017/117575 | 7/2017 |
|---|---|---|
| WO | WO 2017/119003 | 7/2017 |
| WO | WO2019121644 | 6/2019 |

OTHER PUBLICATIONS

International Preliminary Report on Patentability corresponding to International Patent Application No. PCT/EP2018/085444 dated Jun. 23, 2020.
International Search Report corresponding to International Patent Application No. PCT/EP2018/085437 dated Feb. 20, 2019.
International Search Report corresponding to International Patent Application No. PCT/EP2018/085444 dated Feb. 20, 2019.
Katsuyama A. et al., Bull. Spec. CORESTA Symposium, Winston-Salem, 1982, p. 15, So5, ISSN 0525-6240.
Nenajdenko et al., "Synthesis and the Keto-Enol Equilibrium of 2-Acyl Lactams", Russian Chemical Bull., vol. 52, No. 11, pp. 2473-2482 (Nov. 2003).
Pictet, A. (1904) Berichte der deutschen chemischen Gesellschaft, vol. 37, pp. 1225-1235.
Wang J. et al., E. J Med. Chem., 2017, vol. 130, 15-25.
Written Opinion of the International Searching Authority corresponding to International Patent Application No. PCT/EP2018/085437 dated Jun. 27, 2019.
Written Opinion of the International Searching Authority corresponding to International Patent Application No. PCT/EP2018/085444 dated Jun. 27, 2019.
Desai D. et al., J. Labeled Compd. Radiopharm, 2008, vol. 51, 226-230.
Examination Report corresponding to European Patent Application No. 18816112.9 dated May 11, 2021.
Glassco W. et al. (1993) J. Med. Chem. 36, 22, 3381-3385.
Notice of Allowance corresponding to U.S. Appl. No. 16/957,006 dated Apr. 12, 2021.
Notice of Allowance corresponding to U.S. Appl. No. 16/957,006 dated Feb. 2, 2021.
Office Action corresponding to European Patent Application No. 18 816112.9-1110 dated May 11, 2021.
Office Action corresponding to Indian Patent Application No. 202047026902 dated Jan. 18, 2021.
Office Action corresponding to U.S. Appl. No. 16/957,006 dated Oct. 6, 2020.
Search Report corresponding to Russian Patent Application No. 2020120637/04(035217) dated Feb. 15, 2021.
Smirnova et al. "Optical isomerism and biological activity of medicines" Bulletin of Moscow university. Series 2. Chemistry. v.53, N3, 2012, 147-156.
Written Opinion corresponding to Singapore Patent Application No. 11202005641X dated Mar. 29, 2021.
Examination Report corresponding to Australian Patent Application No. 2018391652 dated Jun. 21, 2021.
Notice of Allowance corresponding to U.S. Appl. No. 16/957,006 dated Aug. 27, 2021.
Office Action corresponding to Indian Patent Application No. 202047025938 dated Mar. 22, 2021.
Office Action corresponding to Chilean Patent Application No. 202001656 dated Oct. 26, 2021.
Office Action corresponding to Japanese Patent Application No. 2020-554570 dated Oct. 28, 2021 (machine translation).
Search Report corresponding to Chilean Patent Application No. 202001656 dated Oct. 26, 2021.
Office Action corresponding to Chilean Patent Application No. 202001657 dated Oct. 18, 2021.
Examination Report corresponding to Australian Patent Application No. 2018391657 dated Jun. 21, 2021.
Search Report corresponding to European Patent Application No. 17210187.5 dated May 8, 2018.
Search Report corresponding to Chilean Patent Application No. 202001657 dated Oct. 18, 2021.

* cited by examiner

ENANTIOMERIC SEPARATION OF RACEMIC NICOTINE BY ADDITION OF AN O,O"-DISUBSTITUTED TARTARIC ACID ENANTIOMER

CROSS-REFERENCE TO RELATED APPLICATIONS

This application is a national stage filing of PCT International Application No. PCT/EP2018/085444, filed Dec. 18, 2018, which is based on and claims priority to European Patent Application Serial No. 17210181.8, filed Dec. 22, 2017.

FIELD OF THE INVENTION

The present invention relates to a method of separating nicotine of Formula I-a as a mixture of the (R)- and (S)-enantiomers into the enantiomerically pure substances represented by Formula I-b and Formula I-c.

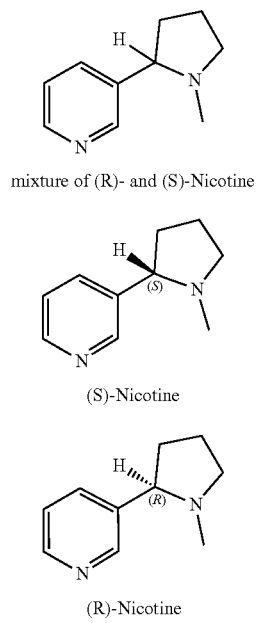

mixture of (R)- and (S)-Nicotine — Formula I-a (S)-Nicotine — Formula I-b (R)-Nicotine — Formula I-c The invention further relates to a method of preparing enantiomerically pure (R)-nicotine and enantiomerically pure (S)-nicotine, where the enantiomers are generally difficult to separate.

BACKGROUND OF THE INVENTION

Nicotine is a naturally occurring alkaloid used in various applications. Especially (S)-nicotine is used as active pharmaceutical ingredient to treat nicotine abuse and nicotine dependency. Success has further been reported when treating Tourette's syndrome, Alzheimer's disease, schizophrenia and other diseases related to disorders of the nervous system. Common ways of administration are gums, creams, transdermal patches, tablets, nasal sprays, and electric cigarettes.

Considerable quantities of nicotine are also used in agriculture as plant protectant or pesticide against aphids.

Natural nicotine is extracted from tobacco plants, a process that requires efficient purification steps to remove undesired, harmful impurities. The increasing demand of nicotine creates a need to offer Ecological and economical ways to prepare synthetic nicotine in, particularly chemically and stereochemically, very pure form.

STATE OF THE ART

Nicotine ((S)-3-(1-methylpyrrolidin-2-yl)pyridine) and its enantiomers have been prepared for many years by various, not satisfying methods. Known syntheses are usually expensive and use agents that harm the environment.

Pictet A. reported in 1904 already a synthesis for nicotine, including the use of tartaric acid to separate the enantiomers (Berichte der deutschen chemischen Gesellschaft, vol. 37, 1904, pages 1225-1235). Tartaric acid has then been used afterwards for decades (see for example: Aceto M. D., et al. (J. Med. Chem., 1979, vol. 22, 17 4-177)).

More recently Chavdarian C. G. et al. disclosed more modern ideas on the synthesis of optically active nicotinoids (J. Org. Chem., 1982, vol. 41, 1069-1073).

Katsuyama A. et al. reported a way of synthesizing nicotine using potassium tert-butanolate for the racemization of nicotine to prepare the starting material for further separation of the enantiomers (Bull. Spec. CORESTA Symposium, Winston-Salem, 1982, p. 15, S05, ISSN.0525-6240).

Further, EP 4 487 172 discloses a synthesis route over 5 different steps, offering a net yield of 37.7%.

In US 2016/0326134 a synthesis of nicotine comprising the condensation of 1-methylpyrrolidin-2-one and methyl nicotinate in the presence of a strong base (as K tert-butoxide) at reflux to the intermediate potassium 1-methyl-3-nicotinoyl-4,5-dihydro-1H-pyrrol-2-olate is described, which then can be converted into the racemic mixture of R/S nicotine. Di-para-toluoyl-L-tartaric acid serves as resolution agent.

EP 2 484 673 (U.S. Pat. No. 8,378,111) relies on well-known routes of synthesis and discloses D-DBTA (D-dibenzoyl ester of tartaric acid) as agent to separate the enantiomers.

WO 2016/065209 (EP 3 209 653, U.S. Pat. No. 9,556,142) discloses a preparative way comprising 3 steps to the intermediate myosmine, including the condensation of N-vinylegous-pyrrolidinone and nicotinate ester in the presence of a metal hydride.

Bowman E. R. et al. describe the preparation of d-nicotine di-(p-toluoly)-L-tartrate from D,L-nicotine using di-(p-toluoyl)-L-tartaric acid monohydrate as separation agent giving an yield of 50% (Synthetic Comm., 1982, vol. 22, 11, 871-879).

Aceto M. D. et al. describe a multi-step resolution process to obtain optically high pure nicotine salts, each step using either pure di-p-toluoyl-D-tartrate or pure di-p-toluoyl-L-tartrate in solvents chosen from methanol, acetone or mixtures thereof (J. Med. Chem, 1979, vol. 2, 22, 174-177).

Glassco W. et al. describe the synthesis and optical resolution of (+)- and (−)-cis-2,3,3a,4,5,9b-hexahydro-1-methyl-1-H-pyrrolo-[3,2-b]isoquinoline (J. Med. Chem. 1993, 36, 22, 3381-3385).

During the last years development was mainly focused on purification and optimization of the resolution step of the optically active enantiomers. But there is still a need for further improvement in this step, particularly towards more efficient, more ecologic synthesis of enantiomerically enriched, essentially pure or even pure (R)- or (S)-nicotine and the use of environmental friendly agents and solvents.

SUMMARY OF THE INVENTION

The current invention offers a novel method for preparing essentially enantiomeric pure (R)- or (S)-nicotine, including a specific process to separate the enantiomers. At the same time increased yield and a high purity of the final product has been found. Overall the novel method is economically and ecologically superior compared to methods known in the art. The inventors found that racemic nicotine can be separated by an inventive method using economically and ecologically advantageous agents. Furthermore, they found that separation of the racemic mixture is also efficient when using separation agents that are not enantiomerically pure.

In a first aspect the present invention provides a method of preparing a compound of Formula I-b, comprising

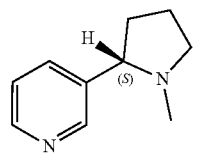
(I-b)

providing nicotine of Formula I-a as a mixture of the (R)- and (S)-enantiomer

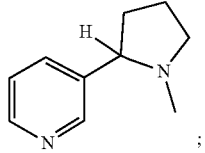
(I-a)

separating enantiomers of the compound of Formula I-a by addition of a chiral O,O'-disubstituted tartaric acid, wherein the chiral O,O'-disubstituted tartaric acid comprises the L-enantiomer; and obtaining the compound of Formula I-b, wherein the O,O'-disubstituted tartaric acid is a mixture of the L-enantiomer and the D-enantiomer, wherein the molar ratio of the L-enantiomer to the D-enantiomer is preferably 80:20 or more, further preferably 90:10 or more, even further preferably 95:5 or more.

Furthermore disclosed is a method of preparing a compound of Formula I-c, comprising

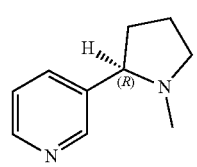
(I-c)

providing nicotine of Formula I-a as a mixture of the (R)- and (S)-enantiomer

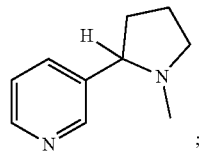
(I-a)

separating enantiomers of the compound of Formula I-a by addition of a chiral O,O'-disubstituted tartaric acid, wherein the chiral O,O'-disubstituted tartaric acid is the D-enantiomer; and obtaining the compound of Formula I-c, wherein the chiral O,O'-disubstituted tartaric acid is O,O'-dibenzoyl-D-tartaric acid.

Further described is a method of preparing a compound of Formula I-b, comprising

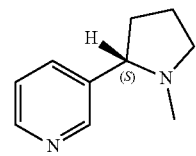
(I-b)

providing nicotine of Formula I-a as a mixture of the (R)- and (S)-enantiomer

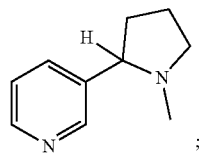
(I-a)

separating enantiomers of the compound of Formula I-a by addition of at least a mixture of two enantiomeric separating agents, wherein one enantiomeric separating agent is preferably used at a molar ratio of 50:50 or more, further preferably 80:20 or more, even further preferably 90:10 or more, even more preferably 95:5 or more, compared to the other enantiomeric separating agent; and obtaining the compound of Formula I-b.

Further embodiments are disclosed in the dependent claims and can be taken from the following description and examples, without being limited thereto.

DETAILED DESCRIPTION OF THE PRESENT INVENTION

If not defined otherwise technical and scientific terms have the same meaning as is generally understood by a skilled person in the field of the invention.

All ranges disclosed herein are to be considered to be supplemented by the term "about", unless clearly defined to the contrary or otherwise clear from the context.

All numbers or percentages relating to amounts of a substance within this application are given in wt. %, unless clearly defined to the contrary or otherwise clear from the context.

Described is a method of preparing a compound of Formula I-b, i.e. (S)-nicotine, is disclosed, comprising

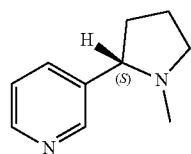

providing nicotine of Formula I-a as a mixture of the (R)- and (S)-enantiomer (I-a)

separating enantiomers of the compound of Formula I-a by addition of a chiral O,O'-disubstituted tartaric acid, wherein the chiral O,O'-disubstituted tartaric acid comprises the L-enantiomer; and obtaining the compound of Formula I-b. In this method the O,O'-disubstituted tartaric acid can consist of the chiral L-enantiomer. In this method the chiral O,O'-disubstituted tartaric acid can further be chosen from O,O'-dibenzoyl tartaric acid (DBTA) and O,O'-ditoluoyl tartaric acid (DTTA), and for example the chiral O,O'-disubstituted tartaric acid can be O,O'-dibenzoyl-L-tartaric acid.

In a first aspect a method of preparing a compound of Formula I-b, i.e. (S)-nicotine, is disclosed, comprising (I-b)

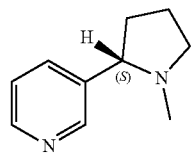

providing nicotine of Formula I-a as a mixture of the (R)- and (S)-enantiomer (I-a)

separating enantiomers of the compound of Formula I-a by addition of a chiral O,O'-disubstituted tartaric acid, wherein the chiral O,O'-disubstituted tartaric acid comprises the L-enantiomer; and obtaining the compound of Formula I-b, wherein the O,O'-disubstituted tartaric acid is a mixture of the L-enantiomer and the D-enantiomer, wherein the molar ratio of the L-enantiomer to the D-enantiomer is preferably 80:20 or more, further preferably 90:10 or more, even further preferably 95:5 or more.

The nicotine of Formula I-a is not particularly restricted and can be obtained in any suitable way, e.g. by extraction from a natural product or by a synthetic method. It is a mixture of the (R)- and (S)-enantiomer of nicotine that is not particularly limited and which can comprise the two enantiomers at any ratio, as long as both enantiomers are contained. It can be a racemic mixture, i.e. a mixture with a molar ratio of 50:50, but it can also be a mixture with a ratio of the (S)-enantiomer to the (R)-enantiomer in the range of e.g. 1:99 to 99:1, e.g. 10:90 to 90:10, e.g. 20:80 to 80:20, e.g. 30:70 to 70:30, e.g. 40:60 to 60:40, e.g. 45:55 to 55:45, or any other ratio in between these ratios. The present method of the first aspect allows the separation of the (S)-enantiomer out of this mixture.

An exemplary synthesis of nicotine of Formula I-a as a racemate ((rac-)nicotine) follows the scheme as presented hereunder in steps 1a, 1b, 1c, and 1d, as also can be found in literature:

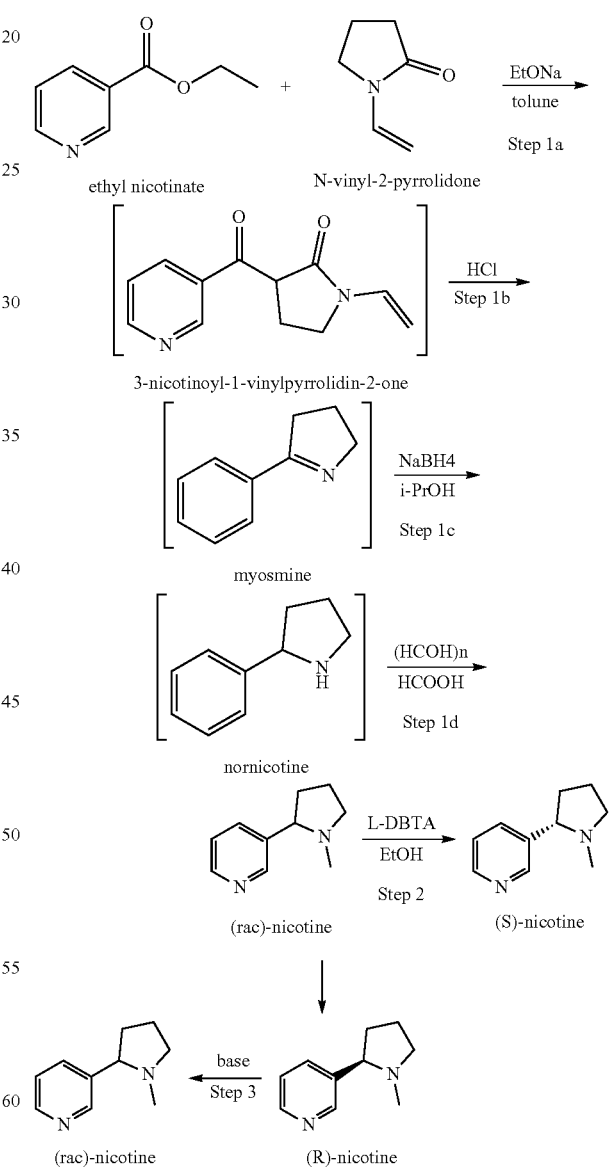

A mixture of (R)- and (S)-nicotine, e.g. racemic nicotine, can be e.g. synthesized, e.g. in a one-pot synthesis with a telescoping method, and generally with a method starting with a condensation of ethyl nicotinate and 1-vinyl-2-pyrrolidone in presence of a base. In the presence of a strong acid the amide nitrogen is deprotected and decarboxylation and ring closure to myosmine takes place. Reduction of the pyrrole ring to a pyrrolidine ring is performed, followed by methylation to nicotine. The mixture of nicotine can be resolved with a resolving agent/separating agent in the method of the first aspect, e.g. L-DBTA, to obtain the target product (S)-nicotine, as shown in step 2. The obtained (R)-nicotine rich side stream can further be recycled by racemization, as shown in step 3, and undergo a further separating/resolving step in line with the method of the first aspect.

In the method of the first aspect the chiral O,O'-disubstituted tartaric acid is not particularly limited as long as it is chiral, i.e. optically active. The two substituents on the oxygen of the hydroxy groups are not particularly limited and can be the same or different. According to certain embodiments they are chosen from alkyl groups with 1 to 20 C-atoms, alkene and/or alkyne groups with 2 to 20 C-atoms, aryl groups with 6 to 20 C-atoms; and/or alkyl aryl and/or aryl alkyl groups with 7 to 20 C-atoms that all can be substituted or unsubstituted by functional groups like halogen groups, nitro groups, amine groups, ester groups, amide groups, etc., and which all are preferably unsubstituted. Preferred substituents in the chiral O,O'-disubstituted tartaric acid are aryl groups with 6 to 20 C-atoms; and/or alkyl aryl and/or aryl alkyl groups with 7 to 20 C-atoms that are not substituted.

According to certain embodiments, the chiral O,O'-disubstituted tartaric acid is chosen from O,O'-dibenzoyl tartaric acid (DBTA) and O,O'-ditoluoyl tartaric acid, e.g. O,O'-di-o-toluoyl tartaric acid, O,O'-di-m-toluoyl tartaric acid and/or O,O'-di-p-toluoyl tartaric acid (DTTA), and or mixtures thereof, preferably O,O'-dibenzoyl tartaric acid. According to certain embodiments, it is added in ethanol as solvent.

In the present method the chiral O,O'-disubstituted tartaric acid comprises the L-enantiomer. The O,O'-disubstituted tartaric comprises the L-enantiomer and the D-enantiomer as a mixture. It is preferable that the L-enantiomer is contained in excess of the D-enantiomer, i.e. at a molar ratio of bigger than 50:50, e.g. at a molar ratio of L-enantiomer to D-enantiomer of at least 80:20, preferably at least 90:10, further preferably 95:5 or more, wherein this ratio can also be described as enantiomeric excess (ee) of at least 60%, preferably at least 80%, further preferably at least 90%.

Described is that the chiral O,O'-disubstituted tartaric acid is O,O'-dibenzoyl-L-tartaric acid, i.e. has an ee of 100%.

According to certain embodiments, the O,O'-disubstituted tartaric acid is added in ethanol as solvent.

While it has been found that the separation of the (R)- and (S)-nicotine can be achieved with a separating agent that is a pure enantiomer, i.e. the L-enantiomer of the chiral O,O'-disubstituted tartaric acid if the (S)-nicotine is to be obtained, it has also surprisingly been found that the same is also accomplished if not a pure separating agent, also termed resolution agent, is used, but also when a mixture of enantiomers of the chiral O,O'-disubstituted tartaric acid is used, which surprisingly achieved the separation effect. Even though pure separating agents/resolution agents are available, there is an advantage in using the economically and ecologically easier accessible agents as mixtures with an excess of one enantiomer, e.g. the L-enantiomer if the (S)-nicotine (compound of Formula I-b) is to be obtained.

The O,O'-disubstituted tartaric acid is a mixture of the L-enantiomer and the D-enantiomer, wherein the L-enantiomer is contained in excess over the D-enantiomer, preferably wherein the molar ratio of the L-enantiomer to the D-enantiomer is 80:20 or more, preferably 90:10 or more, further preferably 95:5 or more. According to certain embodiments, it is added in ethanol as solvent.

According to certain embodiments, the O,O'-disubstituted tartaric acid is a mixture of O,O'-dibenzoyl-L-tartaric acid (L-DBTA) and O,O'-dibenzoyl-D-tartaric acid (D-DBTA) with a molar ratio of L-DBTA to D-DBTA of more than 50:50, preferably 80:20 or more, further preferably 90:10 or more, even further preferably 95:5 or more. According to certain embodiments, it is added in ethanol as solvent.

In the present method, the solvent used for adding the O,O'-disubstituted tartaric acid is not particularly restricted and can be any suitable solvent in which the O,O'-disubstituted tartaric acid can be dissolved. According to certain embodiments, the solvent is ethanol. For the separation, the mixture obtained by adding the O,O'-disubstituted tartaric acid to the compound of Formula I-a can be e.g. refluxed over a certain time period to react the mixture and/or can be stirred under heating, e.g. to a temperature of at least 40° C., preferably 50° C. or more, further preferably 60° C. or more, preferably for at least 15 min, further preferably 30 minutes or more. After such heating a cooling can take place, e.g. to a temperature below 20° C., preferably below 10° C., further preferably below 5° C., preferably for at least 8 hours, preferably at least 10 hours, e.g. 12 hours or more. Also two or more of the reflux and/or heating and optionally cooling steps can be carried out, wherein between each step also seeding with a salt of the S-nicotine and the L-O,O'-disubstituted tartaric acid can take place.

The obtaining of the compound of Formula I-b is not particularly restricted and can be carried out by suitable methods, e.g. hydrolyzing the obtained salt of the (S)-nicotine with the separating agent with water in alkaline medium, extracting with an organic solvent like toluene, and distilling of the solvent. For obtaining the salt of the (S)-nicotine with the separating agent, it can be precipitated beforehand, filtered, and optionally washed, e.g. with ethanol. The steps of precipitating, filtering and washing therein can be carried out repeatedly, e.g. two, three, four or more times.

In a second aspect the present invention relates to a method of preparing a compound of Formula I-c, comprising

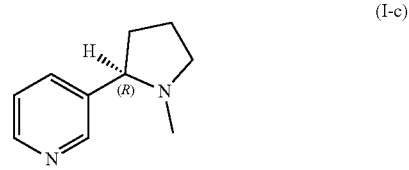

(I-c)

providing nicotine of Formula I-a as a mixture of the (R)- and (S)-enantiomer

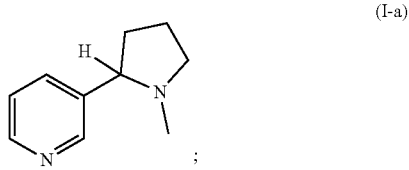

(I-a)

separating enantiomers of the compound of Formula I-a by addition of a chiral O,O'-disubstituted tartaric acid, wherein the chiral O,O'-disubstituted tartaric acid is the D-enantiomer; and obtaining the compound of Formula I-c, wherein the chiral O,O'-disubstituted tartaric acid is O,O'-dibenzoyl-D-tartaric acid.

Again, the nicotine of Formula I-a is not particularly restricted and can be obtained in any suitable way, e.g. by extraction from a natural product or by a synthetic method, as e.g. shown above. It is a mixture of the (R)- and (S)-enantiomer of nicotine that is not particularly limited and which can comprise the two enantiomers at any ratio, as long as both enantiomers are contained. It can be a racemic mixture, i.e. a mixture with a molar ratio of 50:50, but it can also be a mixture with a ratio of the (S)-enantiomer to the (R)-enantiomer in the range of e.g. 1:99 to 99:1, e.g. 10:90 to 90:10, e.g. 20:80 to 80:20, e.g. 30:70 to 70:30, e.g. 40:60 to 60:40, e.g. 45:55 to 55:45, or any other ratio in between these ratios. The present method of the second aspect allows the separation of the (R)-enantiomer out of this mixture.

Described is that the O,O'-disubstituted tartaric acid is chiral, i.e. optically active and contains the D-enantiomer. The two substituents on the oxygen of the hydroxy groups can be the same or different. They can be chosen from alkyl groups with 1 to 20 C-atoms, alkene and/or alkyne groups with 2 to 20 C-atoms, aryl groups with 6 to 20 C-atoms; and/or alkyl aryl and/or aryl alkyl groups with 7 to 20 C-atoms that all can be substituted or unsubstituted by functional groups like halogen groups, nitro groups, amine groups, ester groups, amide groups, etc., and which all are preferably unsubstituted. Preferred substituents in the chiral O,O'-disubstituted tartaric acid are aryl groups with 6 to 20 C-atoms; and/or alkyl aryl and/or aryl alkyl groups with 7 to 20 C-atoms that are not substituted.

Described is that the chiral O,O'-disubstituted tartaric acid can be chosen from O,O'-dibenzoyl-D-tartaric acid and O,O'-ditoluoyl-D-tartaric acid, e.g. O,O'-di-o-toluoyl-D-tartaric acid, O,O'-di-m-toluoyl-D-tartaric acid and/or O,O'-di-p-toluoyl-D-tartaric acid, and or mixtures thereof, preferably O,O'-dibenzoyl-D-tartaric acid.

The chiral O,O'-disubstituted tartaric acid can be added in ethanol as solvent.

In the second aspect the chiral O,O'-disubstituted tartaric acid is O,O'-dibenzoyl-D-tartaric acid, i.e. has an ee of 100%. According to certain embodiments, it is added in ethanol as solvent.

It has been found that the separation of the (R)- and (S)-nicotine can be achieved with a separating agent that is a pure enantiomer, i.e. the D-enantiomer of the chiral O,O'-disubstituted tartaric acid if the (R)-nicotine is to be obtained.

In the present method, the solvent used for adding the O,O'-disubstituted D-tartaric acid is not particularly restricted and can be any suitable solvent in which the O,O'-disubstituted D-tartaric acid can be dissolved. According to certain embodiments, the solvent is ethanol. For the separation, the mixture obtained by adding the O,O'-disubstituted tartaric acid to the compound of Formula I-a can be e.g. refluxed over a certain time period to achieve a clear solution and/or can be stirred under heating, e.g. to a temperature of at least 40° C., preferably 50° C. or more, further preferably 6° C. or more, preferably for at least 15 min, further preferably 30 minutes or more. After such heating a cooling can take place, e.g. to a temperature below 20° C., preferably below 10° C., further preferably below 5° C., preferably for at least 8 hours, preferably at least 10 hours, e.g. 12 hours or more. Also two or more of the reflux and/or heating and optionally cooling steps can be carried out, wherein between each step also seeding with a salt of the R-nicotine and the D-O,O'-disubstituted tartaric acid, i.e. O,O'-dibenzoyl-D-tartaric acid, can take place.

The obtaining of the compound of Formula I-c is not particularly restricted and can be carried out by suitable methods, e.g. hydrolyzing the obtained salt of the (R)-nicotine with the separating agent with water in alkaline medium, extracting with an organic solvent like toluene, and distilling of the solvent. For obtaining the salt of the (R)-nicotine with the separating agent, it can be precipitated beforehand, filtered, and optionally washed, e.g. with ethanol. The steps of precipitating, filtering and washing therein can be carried out repeatedly, e.g. two, three, four or more times.

According to certain embodiments of the second aspect, a seeding with the pure enantiomer, i.e. the (R)-enantiomer, and/or its salt with the O,O'-disubstituted tartaric acid, is carried out, preferably at an increased temperature, further preferably at between 30 and 50° C., particularly preferably at about 40° C., to obtain an increased yield and purity.

Further described is a method of preparing a compound of Formula I-b, comprising

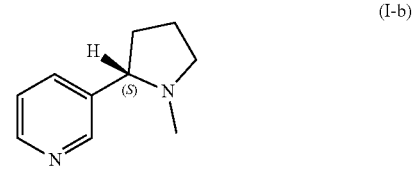

(I-b)

providing nicotine of Formula I-a as a mixture of the (R)- and (S)-enantiomer

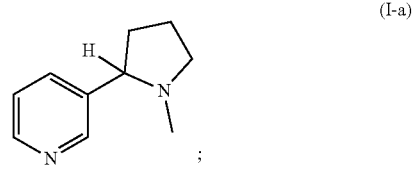

(I-a)

separating enantiomers of the compound of Formula I-a by addition of at least a mixture of two enantiomeric separating agents, wherein one enantiomeric separating agent is used at a molar ratio of 50:50 or more, preferably more than 50:50; further preferably 80:20 or more, even further preferably 90:10 or more, particularly further preferably 95:5 or more, compared to the other enantiomeric separating agent; and obtaining the compound of Formula I-b.

Again, the nicotine of Formula I-a is not particularly restricted and can be obtained in any suitable way, e.g. by extraction from a natural product or by a synthetic method, as e.g. shown above. It is a mixture of the (R)- and (S)-enantiomer of nicotine that is not particularly limited and which can comprise the two enantiomers at any ratio, as long as both enantiomers are contained. It can be a racemic mixture, i.e. a mixture with a molar ratio of 50:50, but it can also be a mixture with a ratio of the (S)-enantiomer to the (R)-enantiomer in the range of e.g. 1:99 to 99:1, e.g. 10:90 to 90:10, e.g. 20:80 to 80:20, e.g. 30:70 to 70:30, e.g. 40:60 to 60:40, e.g. 45:55 to 55:45, or any other ratio in between these ratios. The present method of the third aspect allows the separation of the (S)-enantiomer out of this mixture.

The addition of at least the mixture of two enantiomeric separating agents can be carried out with ethanol as solvent. For the separation, at least the mixture of the two enantiomeric separating agents and the compound of Formula I-a can be e.g. refluxed over a certain time period to react the mixture and/or can be stirred under heating, e.g. to a temperature of at least 40° C., preferably 50° C. or more, further preferably 6° C. or more, preferably for at least 15 min, further preferably 30 minutes or more. After such heating a cooling can take place, e.g. to a temperature below 20° C., preferably below 10° C., further preferably below 5° C., preferably for at least 8 hours, preferably at least 10 hours, e.g. 12 hours or more. Also two or more of the reflux and/or heating and optionally cooling steps can be carried out, wherein between each step also seeding with a salt of the nicotine enantiomer to be obtained and the corresponding O,O'-disubstituted tartaric acid for resolution can take place.

The at least mixture of the two enantiomeric separating agents is not particularly restricted, as long as it contains at least two enantiomers and one enantiomeric separating agent is used at a molar ratio of 50:50 or more, e.g. more than 50:50, preferably 80:20 or more, further preferably 90:10 or more, even further preferably 95:5 or more, compared to the other enantiomeric separating agent. Preferably the two enantiomeric separating agents in the at least a mixture of two enantiomeric separating agents are optical antipodes, i.e. two enantiomers, i.e. two stereoisomers that are mirror images of each other that are non-superposable. The mixture can also contain more than one pair of enantiomeric separating agents, e.g. a mixture of two enantiomers each of two enantiomeric separating agents (e.g. DBTA and DTTA), a mixture of two enantiomers each of three enantiomeric separating agents, etc. with the molar ratios for at least one pair, e.g. at least two pairs, e.g. at least three pairs, etc. of 50:50 or more, e.g. more than 50:50, preferably 80:20 or more, further preferably 90:10 or more, even further preferably 95:5 or more. If two pairs of enantiomeric separating agents are contained, they can be contained in any suitable ratio, e.g. at a molar ratio between 1:4 and 4:1, e.g. between 1:2 and 2:1, e.g. 1:1. Accordingly, mixtures with three pairs of enantiomeric separating agents or more can be contained in any suitable ratio, e.g. at a molar ratio of between 4:1:1, 1:4:1 and 1:1:4, e.g. between 2:1:1, 1:2:1 and 1:1:2, e.g. 1:1:1 for three pairs, etc. Any mixture of suitable enantiomeric separating agents can be applied, e.g. chiral O,O'-disubstituted tartaric acids as described with regard to the first and second aspect of the invention, e.g. chiral O,O'-disubstituted tartaric acids with two acyl substituents, two benzoyl substituents, two toluoyl substituents, with two different substituents, etc., but also others, e.g. D- and L-tartaric acid, as well as mixtures thereof, as indicated above. Preferably, the enantiomeric separating agents are enantiomeric separating agents with a D- and an L-configuration, wherein preferably the L-configuration is used in excess, i.e. at a molar ratio of more than 50:50, preferably 80:20 or more, further preferably 90:10 or more, even further preferably 95:5 or more, compared to the other enantiomeric separating agent in D-configuration.

It has surprisingly been found that a separation of (S)-nicotine is accomplished if not a pure separating agent, also termed resolution agent, is used, but also when a mixture of separating agents is used with an ee given as above, particularly in ethanol as solvent, which surprisingly achieved the separation effect. Even though pure separating agents/resolution agents are available, there is an advantage in using the economically and ecologically easier accessible agents as mixtures with an excess of one enantiomer, e.g. the L-enantiomer if the (S)-nicotine (compound of Formula I-b) is to be obtained.

The obtaining of the compound of Formula I-b is not particularly restricted and can be carried out by suitable methods, e.g. hydrolyzing the obtained salt of the (S)-nicotine with the separating agent with water in alkaline medium, extracting with an organic solvent like toluene, and distilling of the solvent. For obtaining the salt of the (S)-nicotine with the separating agent, it can be precipitated beforehand, filtered, and optionally washed, e.g. with ethanol. The steps of precipitating, filtering and washing therein can be carried out repeatedly, e.g. two, three, four or more times.

In this method a seeding with the pure enantiomer and/or its salt with the enantiomeric separating agent(s) can be carried out, preferably at an increased temperature, further preferably at between 30 and 50° C., particularly preferably at about 40° C., to obtain an increased yield and purity.

The above embodiments can be combined arbitrarily, if appropriate. Further embodiments and implementations of the invention comprise also not explicitly cited combinations of features mentioned beforehand or hereinafter with regard to examples of the invention. Particularly, a skilled person will also add single aspects as improvements or supplements to the respective basic form of the present invention.

EXAMPLES

The present invention will now be described in detail with reference to several examples thereof. However, these examples are illustrative and do not limit the scope of the invention.

Reference Example: General Procedure to Prepare Racemic Nicotine 1.0 eq. of ethyl nicotinate, toluene, 1.6 eq. of sodium ethoxide, and 1.2 eq. of 1-vinyl-2-pyrrolidone (NVP) were charged into a flask at room temperature of about 20° C. under anhydrous conditions. Then the reaction was run at 100° C. for 3 hours. The reaction was completed, and after the mixture had been cooled down to 30° C., 695.0 g HCl (36% by weight in water) was added dropwise. The low boiling components like acetaldehyde, ethanol and the gaseous $CO_2$ were removed by distillation, together with parts of the toluene and the water. When the reaction temperature reached 105° C., distillation was stopped and the reaction mixture was stirred at a temperature between 100° C. and 105° C. overnight. After completion of the reaction, the pH was adjusted to a value between 9.5 to 10.5 using NaOH (30% by weight in water). 360.0 g iso-propanol and 1.0 eq. of $NaBH_4$ (in respect of the ethyl nicotinate) were charged into the reaction vessel. The reaction was run at room temperature (about 20° C.) for more than 3 hours (at this point the content of myosmine was below 3.0% by weight). 2.0 eq. of formic acid (HCOOH, in respect of the ethyl nicotinate) and 1.2 eq. paraformaldehyde ($(HCHO)_n$, in respect of the ethyl nicotinate) were added and the mixture was stirred at 65° C. for at least 3 hours. After the reaction was finished (at this point the content of myosmine was below 0.5% by weight), the pH of the mixture was adjusted to a value of 13 to 14 using NaOH (30% by weight in water). Water was added until all inorganic solids were dissolved.

The mixture was extracted twice with toluene. The combined organic phases were concentrated to obtain the crude product. By distillation of the crude product, racemic nicotine was obtained as a colorless oil with a purity of 98.9% (yield was 66.0%) as sample 1.

Further procedures according to the above with different amounts of reactants and solvents that achieve similar results are shown in Table 1 below:

TABLE 1

Results of a series of reference examples with varying amounts of formic acid and paraformaldehyde

| ethyl nicotinate g | HCl g | i-prop. g | NaBH$_4$ g | HCOOH g | (HCHO)$_n$ g | Yield % | purity % |
|---|---|---|---|---|---|---|---|
| 11.4 (1.0 eq) | 36.0 | 20.0 | 2.86 (1.0 eq) | 10.3 (3.0 eq) | 4.5 (2.0 eq) | 46.0 | 99.7 |
| 11.4 (1.0 eq) | 36.0 | 20.0 | 2.86 (1.0 eq) | 10.3 (3.0 eq) | 4.5 (2.0 eq) | 46.0 | 98.9 |
| 68.4 (1.0 eq) | 216.0 | 48.0 | 17.2 (1.0 eq) | 61.8 (3.0 eq) | 13.5 (1.0 eq) | 51.8 | 99.8 |
| 68.4 (1.0 eq) | 216.0 | 48.0 | 17.2 (1.0 eq) | 61.8 (3.0 eq) | 13.5 (1.0 eq) | 49.6 | 98.7 |
| 68.4 (1.0 eq) | 216.0 | 48.0 | 17.2 (1.0 eq) | 31.0 (1.5 eq) | 16.2 (1.2 eq) | 45.5 | 99.2 |
| 205.2 (1.0 eq) | 648.0 | 360.0 | 51.6 (1.0 eq) | 124.0 (2.0 eq) | 48.6 (1.2 eq) | 47.0 | 95.6 |
| 205.2 (1.0 eq) | 695.0 | 360.0 | 51.6 (1.0 eq) | 124.0 (2.0 eq) | 48.6 (1.2 eq) | 66.0 | 98.9 |
| 205.2 (1.0 eq) | 840.0 | 360.0 | 51.6 (1.0 eq) | 124.0 (2.0 eq) | 48.6 (1.2 eq) | 47.0 | 99.1 |
| 1436.4 (1.0 eq) | 4125.0 | 2500.0 | 432.0 (1.2 eq) | 1312.0 (3.0 eq) | 285.0 (1.0 eq) | 56.0 | 99.1 |
| 1437 (1.0 eq) | 4125.0 | 2500.0 | 432.0 (1.2 eq) | 875.0 (2.0 eq) | 313.0 (1.1 eq) | 59.7 | 97.5 |

In all cases exactly 1.2 eq NVP related to ethyl nicotinate, exactly 1.6 eq EtONa related to ethyl nicotinate, and 60.0 g toluene per 11.4 g ethyl nicotinate were used.

Example 1: Resolution Step 1.0 g racemic nicotine, as obtained by the previous Reference Example, sample 1, was mixed at room temperature with 10 g ethanol (1) and 2.2 g dibenzoyl-L-tartaic acid (L-DBTA) (1 equivalent). The mixture was refluxed for a few minutes and cooled down to room temperature (about 20° C.). Precipitation started, and the mixture was stirred overnight (10 to 12 hours) at 2° C. A precipitate that formed was filtered, washed with 2.5 g ethanol (2). The crude product was dissolved in 5.0 g ethanol (3). The mixture was refluxed for a few minutes and cooled down to room temperature. Precipitation started, and the mixture was stirred overnight (10 to 12 hours) at 2° C. The precipitate was filtered and washed with 2.5 g ethanol (4). The product was dried and the pure product was obtained, Using different amounts as given in Table 2 (samples 2 to 5), similar resolution/separation experiments were carried out. Furthermore, it was found that an increased yield and purity could be obtained with seeding at 40° C.

Example 2

3.2 g nicotine-L-DBTA as produced in Example 1, sample 1, were suspended in 7.2 g water and 7.2 g toluene. Aqueous ammonia (25% by weight) was added until the pH was between 9.8 and 10.4. The phases were separated, and the aqueous phase was extracted twice with 2.4 g toluene. The toluene phases were combined, and toluene was removed by distillation. The residue was distilled under vacuum, yielding 0.93 g pure (S)-nicotine. Enantiopurity was determined by chiral HPLC. The same experiments were carried out with samples 2 to 5 of Example 1, and the results are presented in Table 2.

TABLE 2 samples of Example 1 using various amounts of solvents in steps 1, 2, 3 and 4

| | DBTA 1 g | Ethanol (1) g | Ethanol (2) g | Ethanol (3) g | Ethanol (4) g | Yield | Chiral purity |
|---|---|---|---|---|---|---|---|
| 1 | 100% L-DBTA | 10.0 | 2.5 | 5.0 | 2.5 | 67.6% | 99.8% S-isomer |
| 2 | 100% L-DBTA | 10.0 | 2.5 | 10.0 | 2.5 | 70.8% | 99.6% S-isomer |
| 3 | 98% L_DTBA 2% D-DTBA | 7.5 | 2.5 | 5.0 | 2.5 | 69.8% | 98.2% S-isomer |
| 4 | 95% L_DTBA 5% D-DTBA | 7.5 | 2.5 | 5.0 | 2.5 | 60.0% | 99.6% S-isomer |

TABLE 2-continued samples of Example 1 using various amounts of solvents in steps 1, 2, 3 and 4

| | DBTA 1 g | Ethanol (1) g | Ethanol (2) g | Ethanol (3) g | Ethanol (4) g | Yield | Chiral purity |
|---|---|---|---|---|---|---|---|
| 5 | 90% L_DTBA 10% D-DTBA | 7.5 | 2.5 | 5.0 | 2.5 | 65.3% | 99.6% S-isomer |

Molar equivalents of resolution agent and racemic nicotine have been used. The amount of ethanol is chosen as weight multiple of the racemic nicotine.

Example 3: Alternative Resolution Step 1 g racemic nicotine, as obtained in sample 1 of the Reference example, was mixed at room temperature with 10.0 g ethanol (1) and 2.2 g dibenzoyl-L-tartaric acid (L-DBTA) (1 equivalent). The mixture was heated for a few minutes to 70° C. and stirred for not less than 0.5 hour at 6° C., seeded with (S)-nicotine L-DBTA salt and slowly cooled to 2° C. to 3° C. and stirred overnight. The precipitate formed was filtered and the crude product was dissolved in ethanol (2). The mixture was heated to 75° C. for a few minutes to obtain a clear solution, cooled to 60° C., seeded with (S)-nicotine L-DBTA salt and stirring for 0.5 hours. The obtained suspension is slowly cooled to 2° C. to 3° C. and stirred overnight. The precipitate is filtered off, washed with pre-cooled ethanol (3) and dried under vacuum. (S)-nicotine was produced as in Example 2. The results of different samples 6 to 8 with different amounts of ethanol are shown in Table 3 below.

TABLE 3 samples 6 to 9 of Example 3 using various amounts of solvents in steps 1, 2, 3 and 4

| | DBTA 1 g | Ethanol (1) g | Ethanol (2) g | Ethanol (3) g | Yield | Chiral purity |
|---|---|---|---|---|---|---|
| 6 | 95% L_DTBA 5% D-DTBA | 4.1 | 3.6 | 1.1 | 67.8% | 99.6% S-isomer |
| 7 | 95% L_DTBA 5% D-DTBA | 4.1 | 3.0 | 1.1 | 67.1% | 99.4% S-isomer |
| 8 | 95% L_DTBA 5% D-DTBA | 3.6 | 3.6 | 1.0 | 66.2% | 99.6% S-isomer |

Example 4

Equivalent amounts of dibenzoyl-D-tartaric acid (23.2 g) and racemic nicotine (10 g) were dissolved in ethanol and stirred for 1 hour, refluxed for 15 minutes, cooled to room temperature and stirred for another hour. (R)-nicotine dibenzoyl-D-tartrate was obtained. (R)-nicotine was produced as in Example 2. After recrystallization in an iso-propanol-methanol mixture (1.0:0.3), (R)-nicotine was obtained. The results are given in the following table 4.

TABLE 4 amounts for samples in Example 4

| DBTA | Ethanol | Seeds | Yield | Chiral purity |
|---|---|---|---|---|
| 100% D-DBTA | 10.0 | (R)-nicotine-D-DBTA | 60.0% | 87.9% (R)-isomer |

The invention claimed is:

1. A method of preparing a compound of Formula I-b, comprising

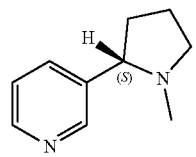

(I-b)

providing nicotine of Formula I-a as a mixture of the (R)- and (S)-enantiomer

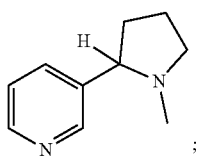

(I-a)

separating enantiomers of the compound of Formula I-a by addition of a chiral O,O'-disubstituted tartaric acid, wherein the chiral O,O'-disubstituted tartaric acid comprises the L-enantiomer and the D-enantiomer; and
obtaining the compound of Formula I-b, wherein the O,O'-disubstituted tartaric acid is a mixture of the L-enantiomer and the D-enantiomer.

2. The method of claim 1, wherein the chiral O,O'-disubstituted tartaric acid is chosen from O,O'-dibenzoyl tartaric acid (DBTA) and O,O'-ditoluoyl tartaric acid (DTTA).

3. The method of claim 1, wherein the O,O'-disubstituted tartaric acid is a mixture of O,O'-dibenzoyl-L-tartaric acid (L-DBTA) and O,O'-dibenzoyl-D-tartaric acid (D-DBTA) with a molar ratio of L-DBTA to D-DBTA of 80:20 or more.

4. The method of claim 1, wherein the addition of the chiral O,O'-disubstituted tartaric acid is carried out with ethanol as solvent.

5. The method of claim 2, wherein the O,O'-disubstituted tartaric acid is a mixture of O,O'-dibenzoyl-L-tartaric acid (L-DBTA) and O,O'-dibenzoyl-D-tartaric acid (D-DBTA) with a molar ratio of L-DBTA to D-DBTA of 80:20 or more.

6. The method of claim 2, wherein the addition of the chiral O,O'-disubstituted tartaric acid is carried out with ethanol as solvent.

7. The method of claim 3, wherein the O,O'-disubstituted tartaric acid is a mixture of O,O'-dibenzoyl-L-tartaric acid (L-DBTA) and O,O'-dibenzoyl-D-tartaric acid (D-DBTA) with a molar ratio of L-DBTA to D-DBTA of 90:10 or more.

8. The method of claim 3, wherein the addition of the chiral O,O'-disubstituted tartaric acid is carried out with ethanol as solvent.

9. The method of claim 1, wherein a molar ratio of the L-enantiomer to the D-enantiomer is 80:20 or more.

10. The method of claim 1, wherein a molar ratio of the L-enantiomer to the D-enantiomer is 90:10 or more.

11. The method of claim 1, wherein a molar ratio of the L-enantiomer to the D-enantiomer is 95:5 or more.

12. The method of claim 3, wherein the O,O'-disubstituted tartaric acid is a mixture of O,O'-dibenzoyl-L-tartaric acid (L-DBTA) and O,O'-dibenzoyl-D-tartaric acid (D-DBTA) with a molar ratio of L-DBTA to D-DBTA of 95:5 or more.

13. The method of claim 5, wherein the O,O'-disubstituted tartaric acid is a mixture of O,O'-dibenzoyl-L-tartaric acid (L-DBTA) and O,O'-dibenzoyl-D-tartaric acid (D-DBTA) with a molar ratio of L-DBTA to D-DBTA of 90:10 or more.

14. The method of claim 5, wherein the O,O'-disubstituted tartaric acid is a mixture of O,O'-dibenzoyl-L-tartaric acid (L-DBTA) and O,O'-dibenzoyl-D-tartaric acid (D-DBTA) with a molar ratio of L-DBTA to D-DBTA of 95:5 or more.

* * * * *

UNITED STATES PATENT AND TRADEMARK OFFICE
CERTIFICATE OF CORRECTION

PATENT NO. : 11,279,685 B2
APPLICATION NO. : 16/956964
DATED : March 22, 2022
INVENTOR(S) : Weber et al.

Page 1 of 1

It is certified that error appears in the above-identified patent and that said Letters Patent is hereby corrected as shown below:

On the Title Page

After the listing of the Assignee(s):
Add --"This patent is subject to a terminal disclaimer."--

Signed and Sealed this
Nineteenth Day of April, 2022

Katherine Kelly Vidal
*Director of the United States Patent and Trademark Office*